(12) United States Patent
Benedict

(10) Patent No.: US 6,524,329 B1
(45) Date of Patent: Feb. 25, 2003

(54) BODY PROCESSING USING LIGHT

(75) Inventor: Mellen-Thomas Benedict, Aptos, CA (US)

(73) Assignee: Tru-Light Corporation, Monterey, CA (US)

( * ) Notice: Subject to any disclaimer, the term of this patent is extended or adjusted under 35 U.S.C. 154(b) by 54 days.

(21) Appl. No.: 09/803,079

(22) Filed: Mar. 8, 2001

(51) Int. Cl.⁷ .............................................. A61N 5/006
(52) U.S. Cl. ......................................... 607/88; 128/828
(58) Field of Search .............................. 607/88–91, 93; 606/3, 9–13; 128/828

(56) References Cited

U.S. PATENT DOCUMENTS

| | | | | |
|---|---|---|---|---|
| 4,930,504 A | * | 6/1990 | Diamantopoulos et al. ...... | 250/494.1 |
| 5,312,396 A | * | 5/1994 | Feld et al. ..................... | 606/10 |
| 5,766,233 A | * | 6/1998 | Thiberg ......................... | 607/88 |
| 5,800,479 A | * | 9/1998 | Thiberg ......................... | 606/2 |
| 6,238,424 B1 | * | 5/2001 | Thiberg ......................... | 606/13 |

* cited by examiner

*Primary Examiner*—Roy D. Gibson
*Assistant Examiner*—Peter Vrettakos
(74) *Attorney, Agent, or Firm*—John F. Schipper

(57) ABSTRACT

Method and system for illuminating a selected body component with light to encourage selected beneficial reactions of the body component as a result of such exposure and to provide phototherapy. The body component is exposed to light in a first wavelength range, in first and second non-overlapping time intervals, and to light within a second wavelength range, in a third time interval that overlaps at least one of the first and second time intervals. The first and second wavelength ranges may be the same, may partly overlap, or may be mutually exclusive and preferably lie within the combined visible and infrared ranges.

24 Claims, 7 Drawing Sheets

BODY PROCESSING USING LIGHT

FIELD OF THE INVENTION

This invention relates to illumination of body components using light with selected wavelength ranges and selected illumination time intervals.

BACKGROUND OF THE INVENTION

Phototherapy involves generation of light by suitable light sources, such as light emitting diodes (LEDs) in the visible and infrared ranges to provide various benefits for a patient's body. The photons produced are absorbed by the body through the skin, the eyes and acupuncture points. Connective tissues in the body conduct the light to deeper tissues and organs. By taking advantage of optical properties of biological tissues, suitable wavelengths of light can be delivered to, absorbed by and used by the body to activate metabolic functions.

Treatment of a body using light irradiation requires a choice of several important parameters, including wavelength range, relative distribution of the wavelengths within the range (spectrum), time interval for continuous exposure, time interval between two continuous exposures, time rate of energy delivered, accumulated energy density for exposures, body component(s) irradiated, and many others. Choice of the appropriate parameters for a given human or animal subject has proved elusive.

What is needed is a method and corresponding system that provides appropriate illumination for a body component and appropriate choice of the relevant parameters and that distinguishes between treatments for different medical purposes. Preferably, the method and system should provide for, and distinguish between, initial treatments and maintenance treatments for a given medical condition and should cover a large number of, if not all of, conditions that are believed to be treatable using illumination.

SUMMARY OF THE INVENTION

These needs are met by the invention, which provides application of radiation in selected wavelength ranges to selected body components using a controlled sequence of exposures. Any two consecutive time intervals of continuous radiation exposure are spaced apart by a "dark field" time interval whose length is at least equal to a threshold value, in order to re-establish a randomization of electron transport and distribution resulting from application of photons during a continuous exposure interval. Radiation is delivered to one or more selected body components, and at selected points on a body, using an enhanced focussing system that increases the efficiency of delivery of the radiation.

DESCRIPTION OF BEST MODES OF THE INVENTION

Figure 1:
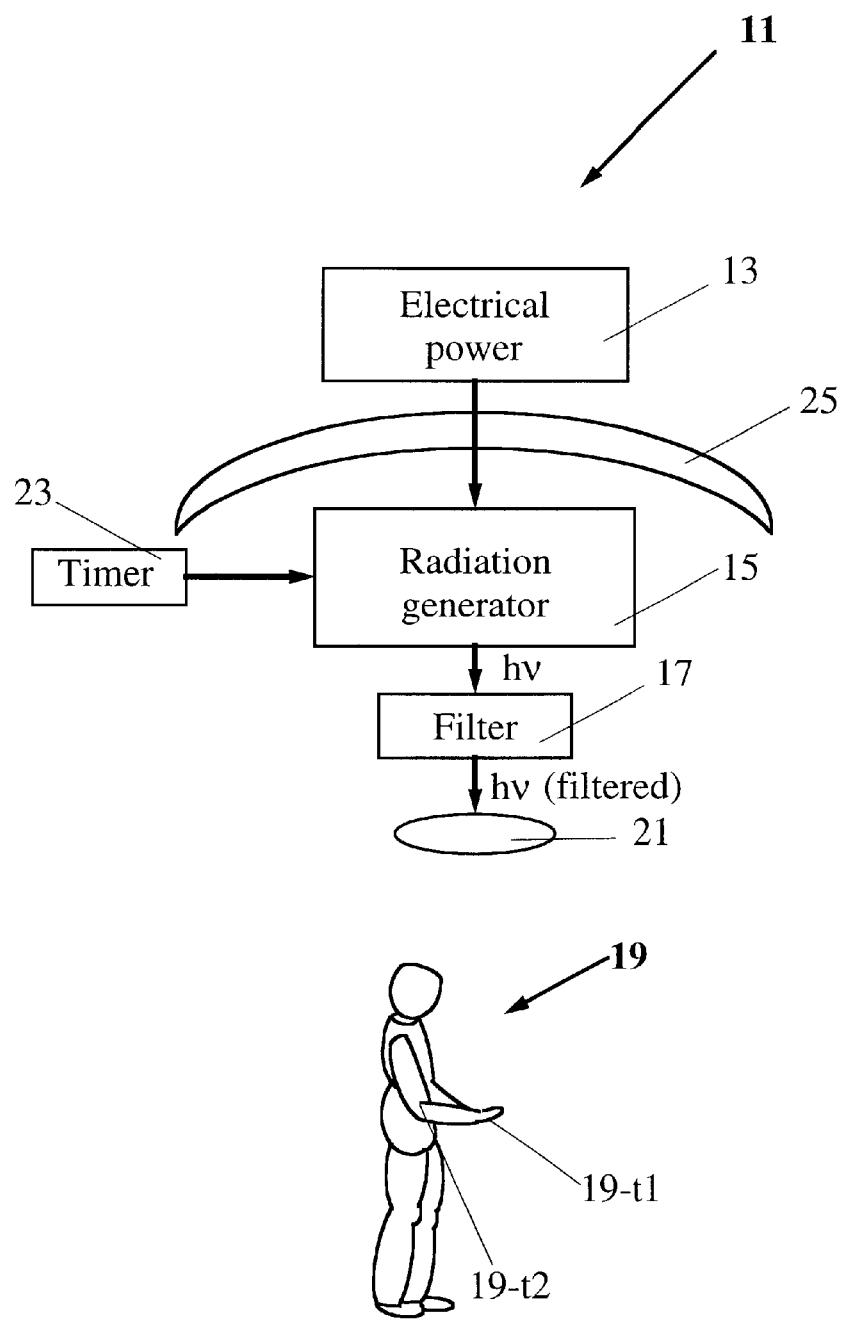
FIG. 1 schematically illustrates apparatus for delivery of radiation to one or more selected body components according to the invention.

FIG. 1 illustrates a system 11 suitable for generating and delivering radiation to one or more selected body components according to the invention. The system 11 includes an electrical power source 13 that delivers controllable power to a generator 15 of electromagnetic radiation in the form of light in the visible and near infrared ranges (e.g., with wavelengths $\lambda$ in a range 400 nm$\leq \lambda \leq$950 nm). Optionally, the light generated by the radiation generator 15 also may have wavelengths in a near-ultraviolet range (e.g., 350 nm$\leq \lambda \leq$400 nm) and may have longer wavelengths in a mid-infrared range (e.g., 950 nm$\leq \lambda \leq$1500 nm), or in selected portions of one or more of these wavelength ranges. The radiation generator 15 may be a laser, a light emitting diode, an intense incandescent light source, an intense fluorescent light source or any other suitable intense light source, or a combination of two or more such light sources. If the generator 15 provides light in one or more unwanted wavelength ranges, one or more filters 17 (optional) may be positioned between the radiation generator 15 and the selected body component(s) 19 to be treated. The radiation generator 15 may produce a single or a few beams of light that are directed toward the body component 19, considered as a target. Preferably, the radiation generator 15 produces many light beams that are directed toward the body component 19. The system optionally includes a light focussing mechanism 21 that preferentially directs light produced by the radiation generator 15 toward one or more target sites 19-tj (j=1, 2, . . . ) On the body component. In some situations, the light beams are produced in a pattern surrounding a selected body part, such as an arm or a leg, so that the selected body part and adjacent body parts are irradiated together in a (diffuse) field effect.

The radiation generator 15 includes a timer 23 that activates and deactivates (turns on and turns off) the radiation generator during selected exposure time intervals, with any two consecutive continuous exposure time intervals having a first selected length $\Delta t(exp)$, separated by a dark field time interval having a second selected length $\Delta t(dark)$. This activity (light/dark/light) and its inverse (dark/light/dark) are sometimes referred to as a "reciprocating chase." The first selected length lies in a preferred range 0.1 sec $<\Delta t(exp)<$1 sec, and the second selected length $\Delta t(dark)$ is preferably between 0.1 sec and 1 sec.

A light reflecting mechanism 25 (optional) is positioned adjacent to the radiation generator 15 to capture and direct light toward the selected body component 19 to couple some or all of the generated light that would otherwise have been lost into that body component. A light concentrator, condenser or other light focussing mechanism 21 (optional) is positioned between the radiation generator 15 and the body component 19, to selectably concentrate (or to scatter within the body) the generated light on and around the body component 19 or selected sites on the selected body component.

Figure 2:
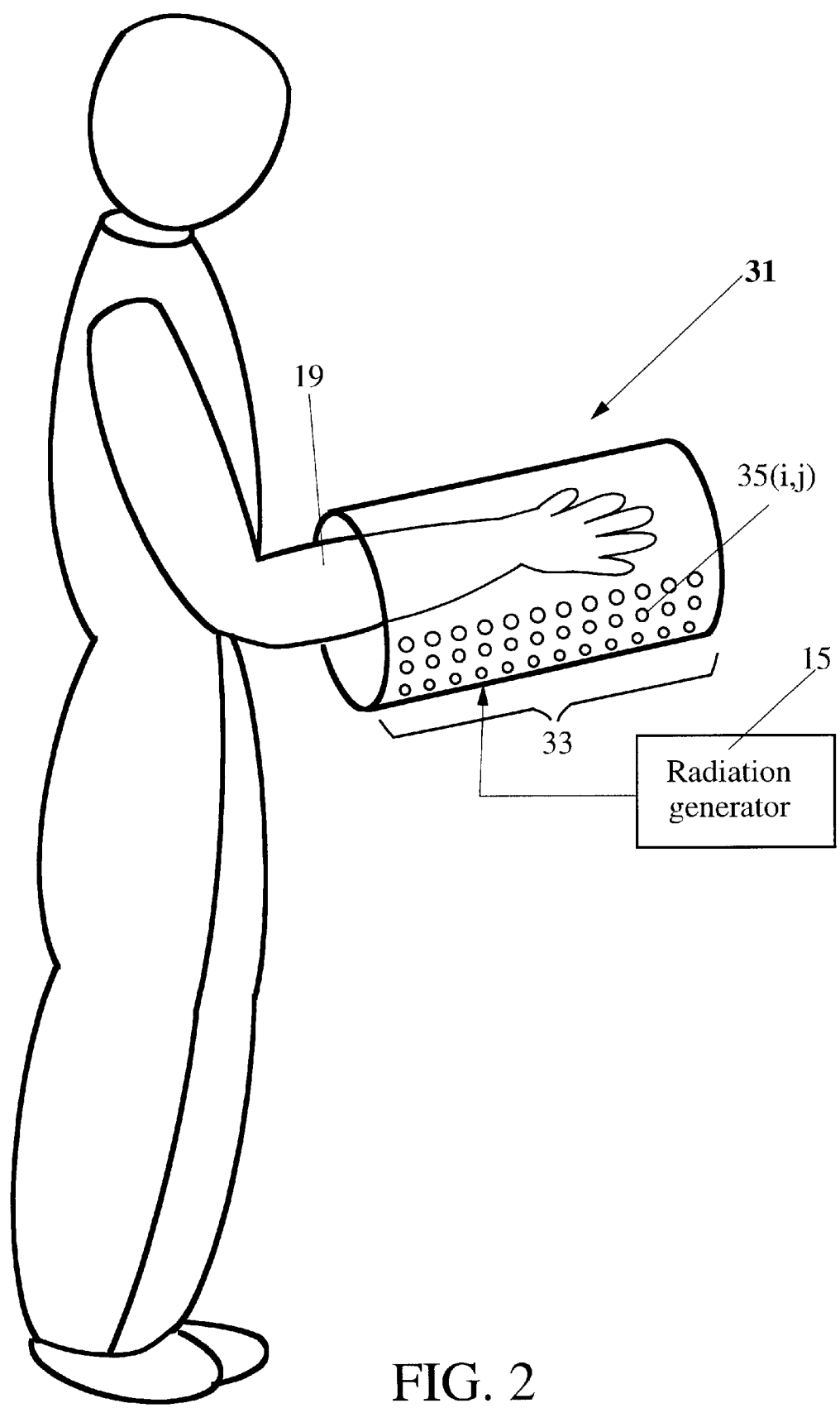
FIG. 2 illustrates a light delivery wrap that can be used to practice the invention.

In one mode of operation, a flexible light delivery wrap 31, illustrated in FIG. 2, is connected to the radiation generator 15 in FIG. 1 and is wrapped around (a portion of) an arm, a leg, a torso, a neck, a head or other body appendage of the patient. The light delivery wrap 31 includes a rectangular, triangular, polygonal, ovular or other array 33 of light delivery elements 35(i,j) (i=1, 2, ..., J1;j=1, 2, ..., J2; J1>1; J2>1) that are individually activated in a timed sequence that may be the same, or different, for each light delivery element. In a first version, where the array 33 is rectangular or triangular, each row of light delivery elements 35(i,j) (i=1, 2, ..., J1; j fixed) is activated and is deactivated as a unit. In a second version, where the array is rectangular or triangular, the light delivery elements 35(i,j) (i=1, 3, 5, ...; j fixed) and 35(i,j) (i=2, 4, 6, ...; j fixed) are activated and are deactivated as separate units. Other patterns for light delivery activation and deactivation can also be used, depending upon the effect desired.

Figure 3:
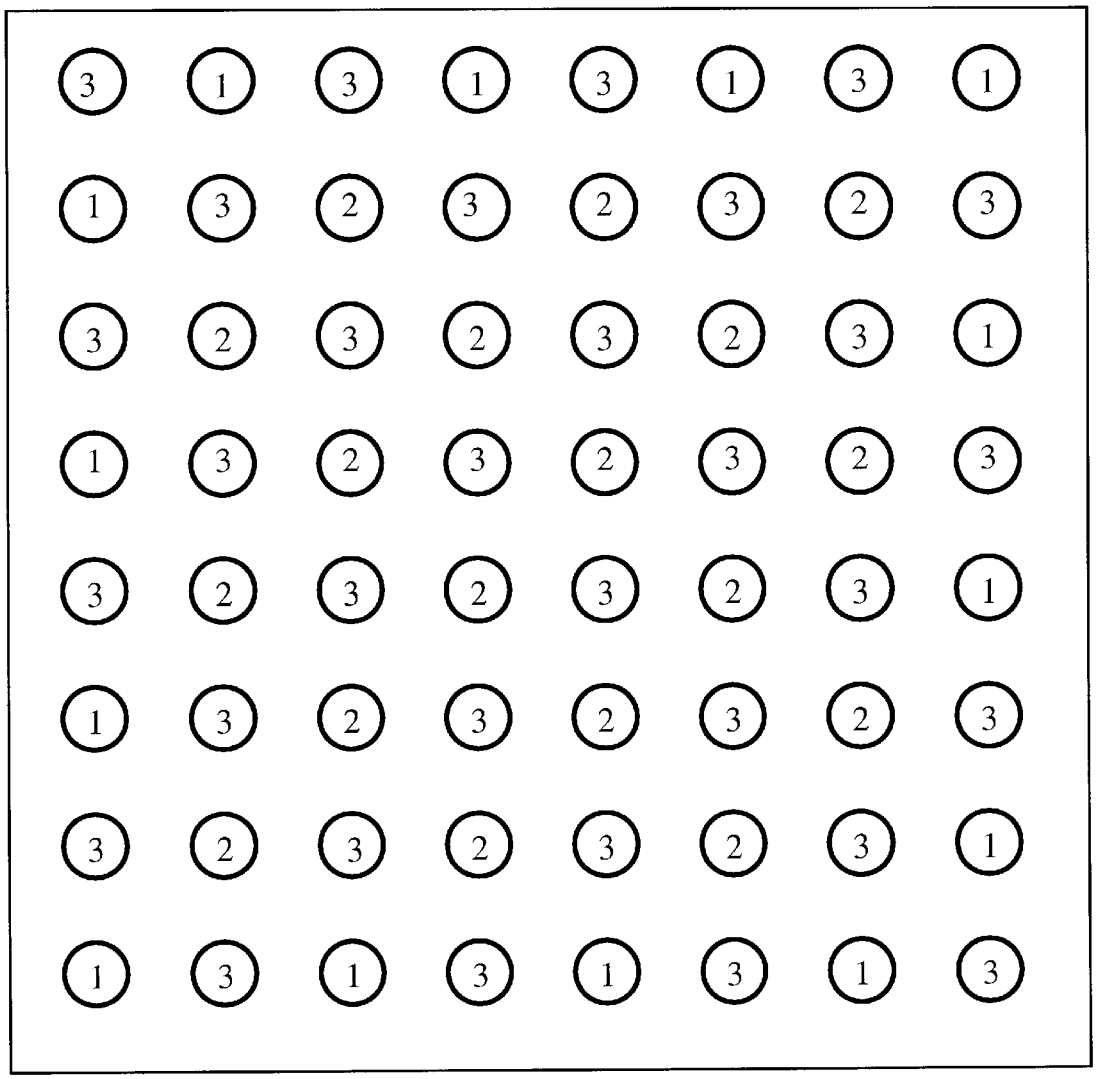
FIG. 3 schematically illustrates a suitable pattern of light sources.

FIG. 3 illustrates a suitable light delivery pattern, in which selected light sources (e.g., light emitting diodes) deliver light in three distinct wavelength ranges (1) a moderately broad band, centered around $\lambda$=550 nm; (2) a moderately broad band, centered around $\lambda$=637 nm; and (3) a narrow band, centered around $\lambda$=890 nm, respectively.

Figure 4A:
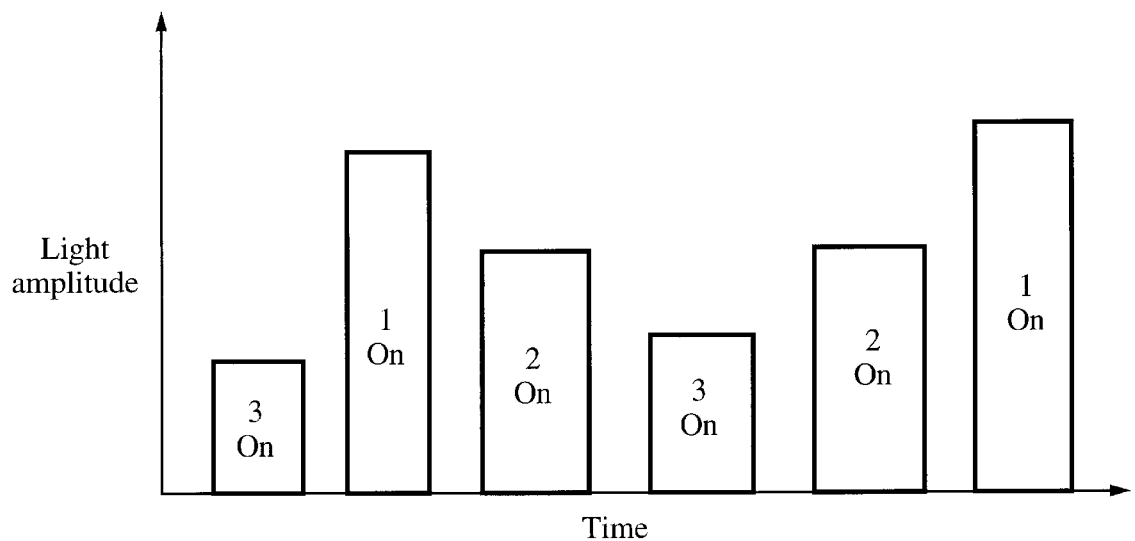
FIGS. 4A and 4B graphically illustrate time intervals for irradiation using different wavelength ranges according to two embodiments of the invention.
Figure 4B:
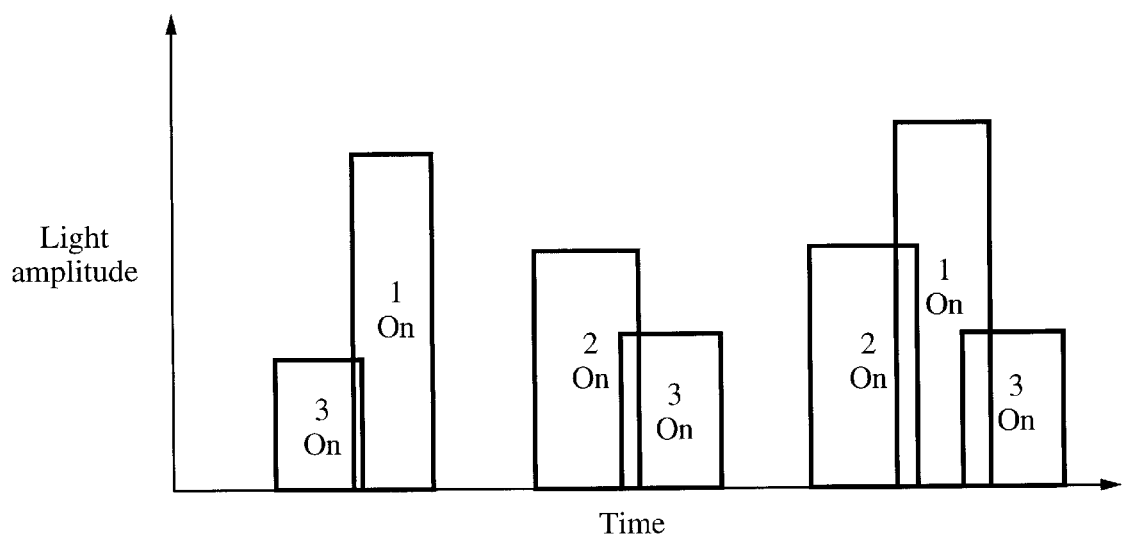

In a preferred embodiment of the invention, the light sources (1), (2) and (3) provide light in different time intervals, with or without a dark field time interval imposed between two consecutive irradiation time intervals. FIG. 4A is a graphical view of time intervals during which the first, second and third light sources (1), (2) and (3) are activated in a nonoverlapping manner. FIG. 4B is a graphical view of a second version, in which the light sources (1), (2) and (3) are activated in selected overlapping time intervals. More generally, N sets of independently activatable light sources (N=3 in FIG. 3) are provided, and N wavelength ranges are chosen within the visible, near-infrared and mid-infrared wavelengths.

Each light delivery element 35(i,j) may deliver light in one or more selected wavelength ranges, when this element is activated, and adjacent light delivery elements may deliver the same, or different, wavelength ranges. In a preferred embodiment, each light delivery element delivers one or more fixed ranges of light wavelengths, such as the ranges 400≦$\lambda$≦550 nm and/or 600 nm≦$\lambda$≦760 nm and/or 800 nm≦$\lambda$≦1500 nm.

Figure 5:
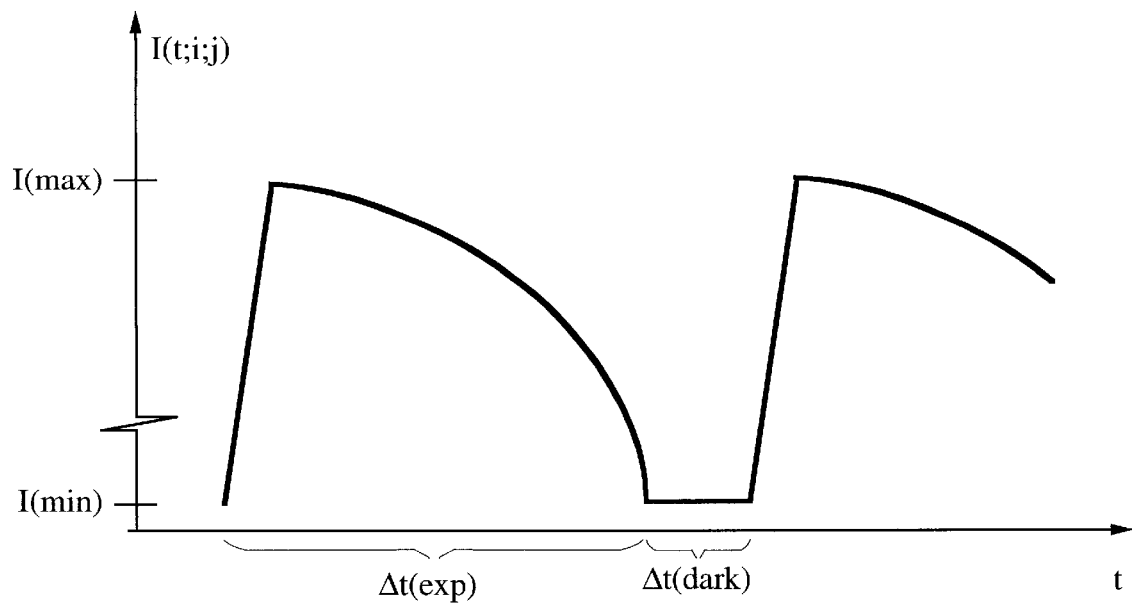
FIGS. 5, 6 and 7 illustrate suitable light intensity patterns versus time for delivery of radiation according to the invention.
Figure 6:
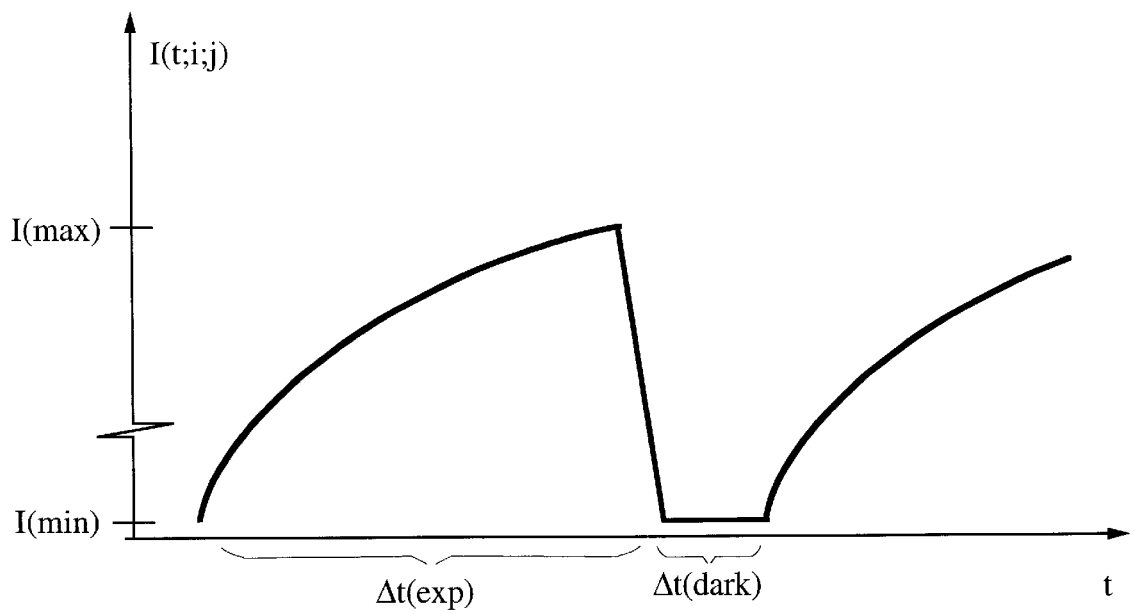
Figure 7:
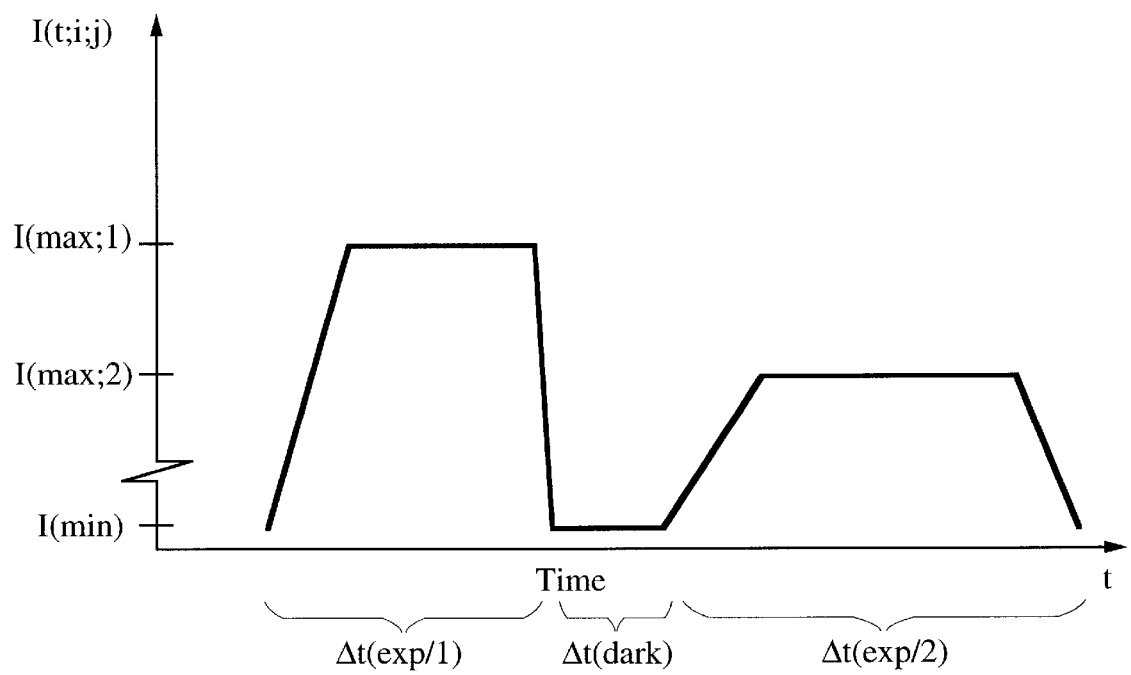

FIGS. 5, 6 and 7 illustrate representative light intensity patterns of light activation (exposure interval) and deactivation (dark field interval) that can be used for the individual light elements 35(i,j) in FIG. 2. In FIG. 5, the light intensity I(t;i;j) is (substantially) 0, then rises quickly to a maximum value I(max), then decreases monotonically to a lower value I(min) over an exposure time interval of length $\Delta$t(exp), then goes to 0 for a dark field time interval of length $\Delta$t(dark), then repeats this pattern at least once. In FIG. 6, the light intensity I(t;i;j) is (substantially) 0, then rises quickly to a minimum value I(min), then increases monotonically to a greater value I(max) over an exposure time interval of length $\Delta$t(exp), then goes to 0 for a dark field time interval of length $\Delta$t(dark), then repeats this pattern at least once. In FIG. 7, the light intensity I(t;i;j) rises to a first maximum value I(max;1), optionally continues at that level for a first selected time interval, falls to a first lower value I(min;1), goes to 0 for a dark field time interval of length $\Delta$t(dark), rises to a second maximum value I(max;2), optionally continues at that level for a second selected time interval, falls to a second lower value I(min;2), then goes to 0. The maximum intensities I(max;1) and I(max;2) may be the same or may differ, the minimum intensities I(min;1) and I(min;2) may be the same or may differ, and one or both of the minimum intensities I(min;1) and I(min;2) may be 0. Light intensity patterns other than the patterns shown in FIGS. 5, 6 and 7 can also be used here.

Figure 8:
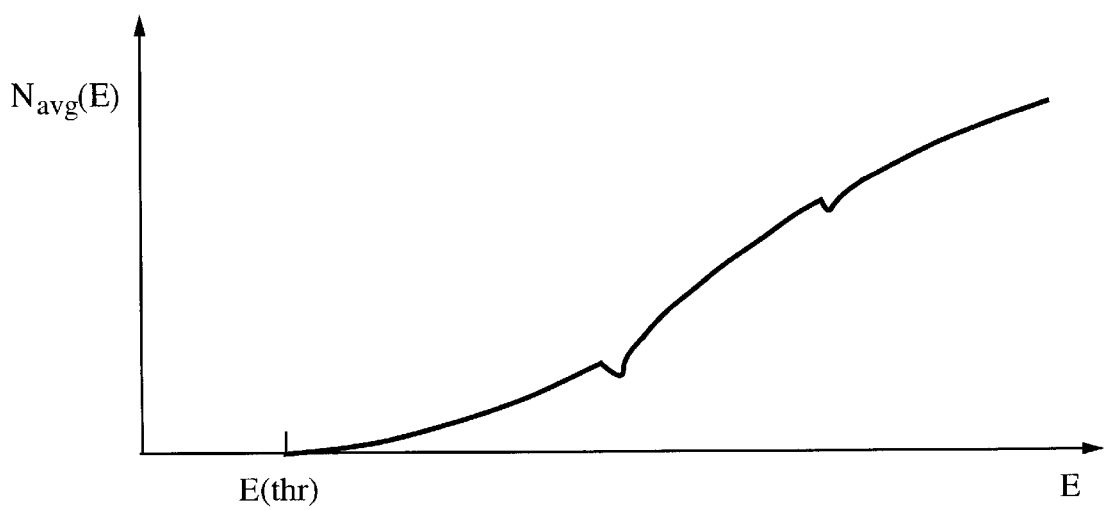
FIG. 8 is a representative graphical view of an average number of free electrons produce by an incident photon with a specified energy E.

Each photon delivered to the vicinity of the body component 19 (FIG. 1) is intended to produce one or more (preferably many) free electrons through photoelectric absorption and/or Compton scattering of the photon in its peregrinations through the body component and surrounding material. We have found, by analogy with the Einstein photoelectric effect in a metallic or crystalline material, that the photon energy E must be at least a threshold value E(thr), which lies in a range of about 1.3–3.1 eV, depending upon the atomic and/or molecular constituents of the selected body component and surrounding material, in order to produce at least one free electron as the photon undergoes scattering within the body. A photon with a wavelength $\lambda$=500 nm has an associated energy of 2.48 eV, for example, and the wavelength range 400 nm≦$\lambda$≦950 nm corresponds to an energy range 1.31 eV≦E≦3.10 eV. Not all photons with energies E just above the threshold value E(thr) will produce a free electron. A graph of average number $N_{avg}(E)$ of free electrons produced for a given incident photon energy E might resemble the graph in FIG. 8. This graph is similar to a graph of average number of free electrons produced by a photon incident on a metallic or crystalline material according to the Einstein model.

Another important parameter is the rate r at which energy (or photons) is delivered to a unit area (e.g., over 1 cm$^2$) of body surface per unit time (e.g., in 1 sec), during an exposure time interval. Our experiments indicate that energy density rates r in a range 0.0013 Joules/cm$^2$/sec≦r≦0.02 Joules/cm$^2$/sec, averaged over a time interval of 5–45 min, is an appropriate range for many body components for green light ($\lambda$≈550 nm), red light ($\lambda$≈637 nm), white light and/or infrared light ($\lambda$≈890 nm). Delivery of energy at a rate lower than about 0.0013 Joules/cm$^2$/sec will have some effect but will require much longer radiation application times than a typical application time of 5–45 min. Delivery of energy at a rate greater than about 0.02 Joules/cm$^2$/sec may saturate the body's ability to distribute the photon energy and may produce burns, ionization or other undesired local sensitization of the body. The peak light intensity I(t;i;j), shown in the examples of FIGS. 5, 6 and 7, will determine, or will be determined by, the energy rate r.

Another important parameter is accumulated energy E(accum) delivered per unit area for the session in which radiation is applied. Our experiments indicate that an accumulated energy density range of 2.5 Joules/cm$^2$≦E(accum) ≦20 Joules/cm$^2$ is an appropriate range for many body components. Delivery of accumulated energy density greater than 20 Joules/cm$^2$ may produce burns, ionization or other undesired local sensitization of the body.

Figure 9:
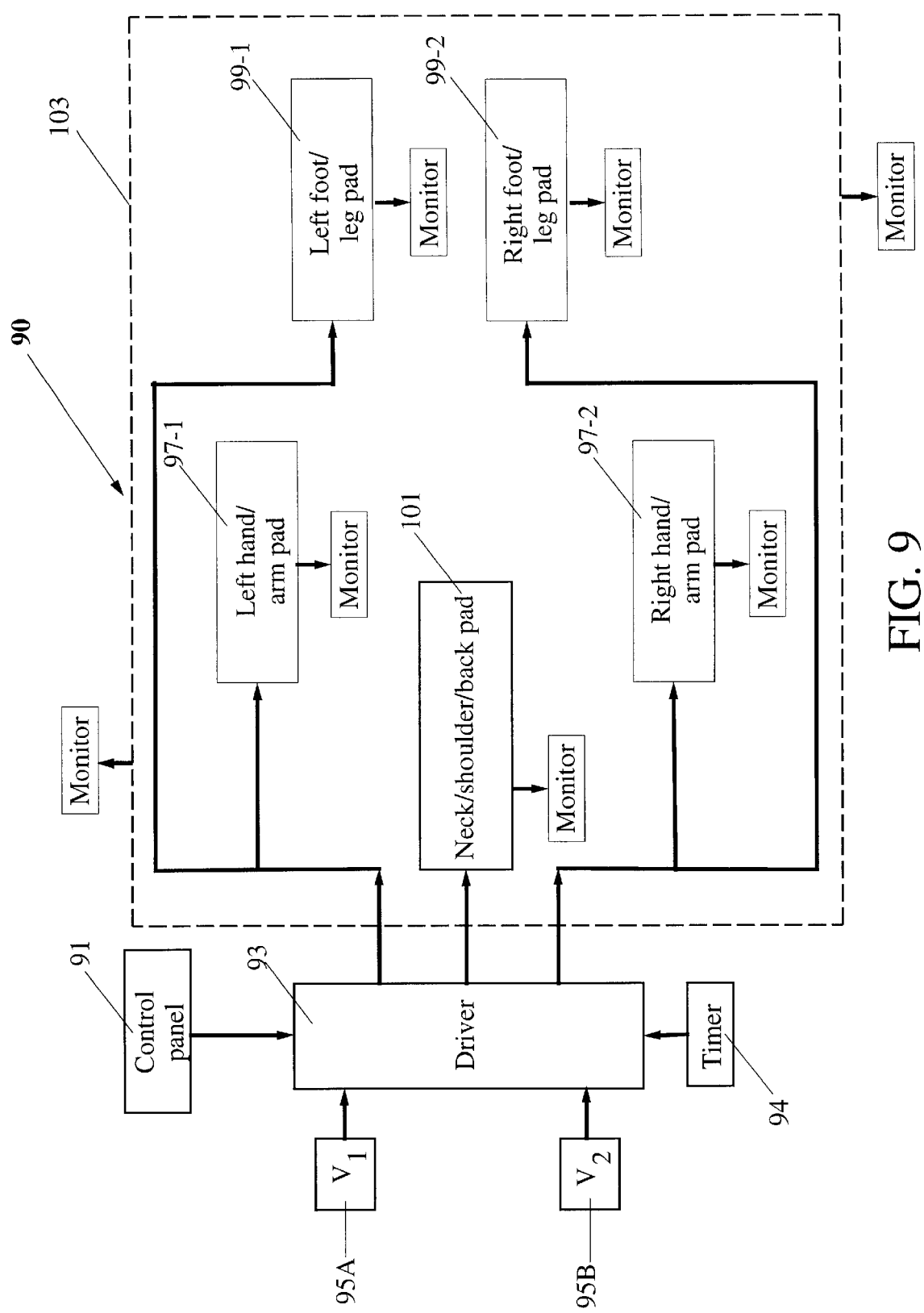
FIG. 9 is a schematic view illustrating apparatus that can be used to practice the invention.

FIG. 9 schematically illustrates apparatus 90 that can be used to practice the invention. A control panel 91 controls the exposure time intervals, the dark field time intervals, the maximum intensity(ies), the particular intensity pattern(s) to be applied, the wavelength or frequency range(s) to be applied, target body component(s) and/or other relevant parameters, through control panel output signals delivered to a driver module 93. The driver module receives timing signals from a timer module 94 and receives electrical power (preferably regulated power) from one or more voltage sources, 95A and/or 95B, that deliver voltage(s), V1 and/or V2, or electrical current. At least one of the control panel 91 and the driver module 93 includes a computer to process information and/or commands needed to provide appropriate light wavelengths in the appropriate time intervals according to the invention. The driver module 93 delivers power to one or more of a left hand/arm exposure pad 97-1, a left foot/leg exposure pad 99-1, a right hand/arm exposure pad 97-2, a right foot/leg exposure pad 99-2 a neck/shoulder(s)/back exposure pad 101, and/or a light exposure canopy 103 covering part or all of a patient's body, each of which has an optional associated cumulative exposure monitor and/or exposure rate monitor connected to the corresponding exposure pad or exposure canopy. Optionally, one or more of these exposure pads may have its own electrical power supply, received directly from the driver module 93. The exposure pads are individually controlled and can deliver different (or the same) exposure patterns and different (or the same) wavelength ranges to target body components associated with the different exposure pads, in the same time intervals or in different time intervals. In some situations, it is appropriate to provide at least two voltages sources, such as V1=5 volts and V2=12 volts.

We have found that insertion of a dark field time interval between two consecutive continuous exposure time intervals is useful in allowing the irradiated portion of the body to re-establish local equilibrium before the next pulse of photons arrives. The time interval required for re-establishing local equilibrium appears to vary from 0.1 sec to about 1 sec, depending upon variables such as the energy rate r, the accumulated energy E(accum) and the selected body component(s) irradiated. If the dark field time interval has a length less than $\Delta t(dark)$ (including a situation where no dark field interval is present), the additional photons delivered may encounter a body environment that is not at or near equilibrium and that "channels" these photons in particular directions or into particular reaction channels, which is generally undesirable. Where two consecutive exposure time intervals are separated by a dark field time interval of length at least $\Delta t(dark)$, the irradiated portion of the body is able to re-establish local equilibrium, or near-equilibrium, so that most or all photons within a given exposure time interval encounter substantially the same local environment, and a random or Monte Carlo type of photon scattering occurs within the next exposure time interval.

The free electrons thus produced ultimately come to equilibrium with the body component and adjacent material within the body, by attachment to a atom or molecule that can support attachment by another electron or by association with a assembly of substantially-free electrons that are weakly bound by the general electronic background of the local atomic and molecular constituents of the body. These equilibrated electrons have transferred substantially all their initial kinetic energy to one or more molecules in or adjacent to the body component, thus providing energy to promote certain healing processes in the body.

Phototherapy is the application of light from an artificial light source to stimulate or promote one or more therapeutic effects in the body of a human being or other animal. Photons from the, light source are absorbed by the body through the skin, through the eyes and through acupuncture points. Light absorbed through one or more acupuncture points is believed to be transported especially efficiently along channels, referred to as biologically closed electrical paths or "meridians", in the body, through a process similar to internal reflection of light in an optical fiber (whose refractive index is greater than the refractive index of the surrounding body material through which such a channel passes. These channels are believed to be connective tissue protein fibers having specialized optical properties, including refractive indices $\eta$ that are greater than the refractive indices $\eta'$ of surrounding tissues, organs and other body material (wherein $\eta'(avg) \approx 1.4$).

Only light in certain wavelength ranges will be transported efficiently through these channels. Absorption of light transported in one or more of these channels has the potential to increase cell metabolism from a depressed state to a normal level. Light in the 600–800 nm wavelength range appears to be transported with little absorption or scattering within these channels. Sergei Pankratov, of the Institute for Clinical and Experimental Medicine in Novosibirsk, Russia, has reported that marked light transporting properties of some of these channels, which easily transport light into tissues deeper within the body, "Meridians Conduct Light", Raum und Zeit, vol. 35(88) (1991) pp. 16–18. A terminus on the skin of such a channel often coincide, with an acupuncture point identified by Chinese physicians several millenia ago. In addition to its optical properties, a light transport channel has associated thermal properties, such as heat conductivity and heat capacity.

Phototherapy activates cell membranes within the body by increasing a membrane's natural electrical charge, sometimes referred to as "membrane capacitance." A body's natural electromagnetic field ("biofield") aids in organizing molecular structures in repair, regeneration and reproduction of cells and cell components and serves as a signal communication system in regulation of metabolic processes. The biofield may also serve as a power grid to provide electrical and/or chemical energy to drive and control biochemical and biphysical enzyme reactions that are part of a metabolic process. One such process is: (1) receipt and conversion of light in a channel; (2) activation of cell enzymes; and (3) enhanced production of adenosine triphosphate (ATP) from the activated enzymes, as the primary energy source for a body.

One researcher, Tiina Karu has determined that light absorption by cellular structures enhances a number of cell-related activities: cell replication, cell metabolism, protein synthesis, ATP production, mitochondria replication, phagocytosis, and photodissociation of oxygenated hemoglobin (*The Science of Low-Power Laser Therapy*, Gordon and Breach, 1998, "Photobiology of Low Power Laser Effects", Health Physics, vol. 56, May 1989). Karu has also found that absorption of light affects tissue-related activities, including: capillary formation, parasympathetic nervous system stimulation, increased endorphin release, increased production and release of adrenal steroids, reduction in pain and in inflammation, reduction of tissue edema, immune system stimulation, enhanced fibroblastic production and collagen synthesis, and accelerated healing of wounds.

What is claimed is:

1. A method of illuminating a human's body, the method comprising:

exposing a selected component of a human's body to light having a first selected range of wavelengths for a first selected exposure time interval and for a second selected exposure time interval, where the first and second time intervals are spaced apart by a first dark time interval having a selected length $\Delta t(dark;1)$ that is at least 0.1 sec, and allowing light received in at least one of the first time interval and the second time interval to produce at least one free electron within or adjacent to the body component;

exposing the body component to light having a second selected range of wavelengths for a third selected exposure time interval, and allowing light received in the third time interval to produce at least one free electron within or adjacent to the body component, where at least one of the first and second time intervals overlaps the third time interval by an overlap time interval having a positive overlap length; and allowing the at least one free electron produced during the at least one of the first and second exposure time intervals and during the third interval to come to equilibrium with the body adjacent to or within the body component.

2. The method of claim 1, further comprising choosing said first and second wavelength ranges to have substantially no wavelength overlap.

3. The method of claim 1, further comprising choosing at least one of said first wavelength range and said second wavelength range to be contained in an overall wavelength range 400 nm$\leq\lambda\leq$950 nm.

4. The method of claim 3, further comprising choosing at least one of said first and second wavelength ranges to include at least one of the wavelengths $\lambda$=550 nm, $\lambda$=637 nm and $\lambda$=890 nm.

5. The method of claim 1, further comprising choosing at least one of said first and second wavelength ranges to lie within a visible wavelength range (400 nm$\leq\lambda\leq$760 nm) or within an infrared wavelength range ($\lambda$>760 nm).

6. The method of claim 1, further comprising exposing said body component to said light having an energy density rate r lying in a range 0.0013 Joules/cm$^2$/sec $\leq$r$\leq$0.02 Joules/cm$^2$/sec, during at least one of said first time interval, said second time interval and said third time interval.

7. The method of claim 1, further comprising exposing said body component to said light having an accumulated energy density E(accum) lying in a range 2.5 Joules/cm$^2\leq$E(accum)$\leq$20 Joules/cm$^2$.

8. The method of claim 1, further comprising choosing a length $\Delta$t(exp) for at least one of said first time interval, said second time interval and said third time interval to lie in a range 0.1 sec$\leq\Delta$t$\leq$1 sec.

9. A system for illuminating a human's body, the system comprising:

a light source for generating and focusing light to expose a selected component of a human's body to light having a first selected range of wavelengths for first and second selected exposure time intervals, and to expose the body component to light having a second selected range of wavelengths for a third selected exposure time interval, where the first and second time intervals are spaced apart by a first dark time interval having a selected length $\Delta$t(dark;1) that is at least 0.1 sec and at least one of the first and second time intervals overlaps the third time interval by an overlap time interval having a positive overlap length;

where light received in at least one of the first time interval and the second time interval is allowed to produce at least one free electron within or adjacent to the body component and light received in the third time is allowed to produce at least one free electron within or adjacent to the body component; and where the at least one free electron produced during the at least one of the first and second exposure time intervals and during the third time interval is allowed to come to equilibrium with the body adjacent to or within the body component.

10. The system of claim 9, wherein said first and second wavelength ranges are chosen to have substantially no wavelength overlap.

11. The system of claim 9, wherein at least one of said first wavelength range and said second wavelength range is contained in an overall wavelength range 400 nm$\leq\lambda\leq$950 nm.

12. The system of claim 11, wherein at least one of said first and second wavelength ranges includes at least one of the wavelengths $\lambda$=550 nm, $\lambda$=637 nm and $\lambda$=890 nm.

13. The system of claim 9, wherein at least one of said first and second wavelength ranges lies within a visible wavelength range (400 nm$\leq\lambda\leq$760 nm) or within an infrared wavelength range ($\lambda$>760 nm).

14. The system of claim 9, wherein said body component is exposed to said light having an energy density rate r lying in a range 0.0013 Joules/cm$^2$/sec$\leq$r$\leq$0.02 Joules/cm$^2$/sec, during at least one of said first time interval, said second time interval and said third time interval.

15. The system of claim 9, wherein said body component is exposed to said light having an accumulated energy density E(accum) lying in a range 2.5 Joules/cm$^2\leq$E(accum)$\leq$20 Joules/cm$^2$.

16. The system of claim 9, wherein a length $\Delta$t(exp) for at least one of said first time interval, said second time interval and said third time interval is chosen to lie in a range 0.1 sec$\leq\Delta$t$\leq$1 sec.

17. The method of claim 1, further comprising providing said light during at least one of said first and second exposure time intervals at a first selected light intensity, and providing said light during said third exposure time interval at a second selected light intensity, where the second light intensity is no greater than about one-half of the first light intensity.

18. The method of claim 1, further comprising providing said light during said first and second exposure time intervals at first and second selected light intensities that differ from each other.

19. The method of claim 6, further comprising providing said light in said first range of wavelengths over a time interval of length in a range 5–45 minutes.

20. The method of claim 6, further comprising providing said light in said second range of wavelengths over a time interval of length in a range 5–45 minutes.

21. The system of claim 9, wherein said light source provides said light during at least one of said first and second exposure time intervals at a first selected light intensity and provides said light during said third exposure time interval at a second selected light intensity, where the second light intensity is no greater than about one-half of the first light intensity.

22. The system of claim 9, wherein said light source provides said light during said first and second exposure time intervals at first and second selected light intensities that differ from each other.

23. The system of claim 14, wherein said light source provides said light in said first range of wavelengths over a time interval of length in a range 5–45 minutes.

24. The system of claim 14, wherein said light source provides said light in said second range of wavelengths over a time interval of length in a range 5–45 minutes.

* * * * *